United States Patent
Pelletier et al.

(10) Patent No.: US 9,433,473 B2
(45) Date of Patent: *Sep. 6, 2016

(54) TOOL AND METHOD FOR DIGITAL ACQUISITION OF A TIBIAL MECHANICAL AXIS

(71) Applicant: ORTHOSOFT INC., Montreal (CA)

(72) Inventors: Benoit Pelletier, Laval (CA); Karine Duval, Montreal (CA); Trong Tin Nguyen, Laval (CA); Pierre Couture, Montreal (CA); Louis-Philippe Amiot, Hampstead (CA); Yannick Boutin, Montreal (CA); Alain Richard, Lachine (CA); Catherine Proulx, Verdun (CA)

(73) Assignee: ORTHOSOFT INC., Montreal (CA)

( * ) Notice: Subject to any disclaimer, the term of this patent is extended or adjusted under 35 U.S.C. 154(b) by 207 days.

This patent is subject to a terminal disclaimer.

(21) Appl. No.: 14/016,579

(22) Filed: Sep. 3, 2013

(65) Prior Publication Data
US 2014/0005673 A1    Jan. 2, 2014

Related U.S. Application Data

(63) Continuation of application No. 12/872,469, filed on Aug. 31, 2010, now Pat. No. 8,551,108.

(51) Int. Cl.
*A61B 17/15* (2006.01)
*A61B 19/00* (2006.01)
*A61B 5/00* (2006.01)

(52) U.S. Cl.
CPC ......... *A61B 19/5244* (2013.01); *A61B 17/157* (2013.01); *A61B 5/4528* (2013.01);

(Continued)

(58) Field of Classification Search
CPC ...... A61F 2/4657; A61B 19/46; A61B 19/50
See application file for complete search history.

(56) References Cited

U.S. PATENT DOCUMENTS 4,841,975 A    6/1989 Woolson
5,197,944 A    3/1993 Steele
(Continued)

FOREIGN PATENT DOCUMENTS

DE    10045381    4/2002
DE    102004061764    7/2006
(Continued)

OTHER PUBLICATIONS

Extended European Search Report, EP Application No. 10856542.5, May 25, 2016.

*Primary Examiner* — Nicholas Woodall
(74) *Attorney, Agent, or Firm* — Norton Rose Fulbright Canada LLP

(57) ABSTRACT

A tool for digitizing a mechanical axis of a tibia using a computer-assisted surgery system is described. The tool includes upper and lower mounting ends interconnected by an alignment rod extending therebetween. The upper mounting end is releasably fastenable to an upper reference point on a tibial plateau and the lower mounting end includes a self-centering malleoli engaging mechanism having opposed caliper arms displaceable in a common plane relative to each other for clamping engagement with the medial and lateral malleoli of the ankle. At least one trackable member is mounted to the alignment rod of the tool and is in communication with the computer assisted surgery system for providing at least orientation information of the alignment rod. The mechanical axis of the tibia is parallel to the alignment rod and extends between the upper and lower reference points when the tool is mounted on the tibia.

24 Claims, 14 Drawing Sheets

(52) U.S. Cl.
CPC .......... *A61B 5/4538* (2013.01); *A61B 5/4585* (2013.01); *A61B 17/154* (2013.01); *A61B 2034/2048* (2016.02); *A61B 2034/2068* (2016.02)

(56) References Cited

U.S. PATENT DOCUMENTS

| | | | |
|---|---|---|---|
| 5,611,353 | A | 3/1997 | Auchinleck et al. |
| 5,704,941 | A | 1/1998 | Jacober et al. |
| 5,971,976 | A | 10/1999 | Wang et al. |
| 6,090,114 | A | 7/2000 | Matsuno et al. |
| 6,122,538 | A | 9/2000 | Sliwa et al. |
| 6,267,762 | B1 | 7/2001 | Millard et al. |
| 6,490,467 | B1 | 12/2002 | Bucholz et al. |
| 6,786,877 | B2 | 9/2004 | Foxlin |
| 7,065,393 | B2 | 6/2006 | Sati et al. |
| 7,277,594 | B2 | 10/2007 | Hofstetter et al. |
| 7,708,741 | B1 | 5/2010 | Bonutti |
| 2003/0069591 | A1 | 4/2003 | Carson et al. |
| 2004/0039396 | A1 | 2/2004 | Couture et al. |
| 2004/0102785 | A1 | 5/2004 | Hodorek et al. |
| 2004/0230199 | A1 | 11/2004 | Jansen et al. |
| 2004/0243148 | A1 | 12/2004 | Wasielewski |
| 2005/0113646 | A1 | 5/2005 | Sotos et al. |
| 2005/0143676 | A1 | 6/2005 | De Guise et al. |
| 2007/0032723 | A1 | 2/2007 | Glossop |
| 2007/0100346 | A1 | 5/2007 | Wyss et al. |
| 2007/0287901 | A1 | 12/2007 | Strommer et al. |
| 2007/0287911 | A1 | 12/2007 | Haid et al. |
| 2008/0039868 | A1 | 2/2008 | Tuemmler et al. |
| 2008/0051910 | A1 | 2/2008 | Kammerzell et al. |
| 2008/0065084 | A1 | 3/2008 | Couture et al. |
| 2009/0248044 | A1 | 10/2009 | Amiot et al. |
| 2010/0063508 | A1 | 3/2010 | Borja et al. |
| 2010/0137869 | A1 | 6/2010 | Borja et al. |

FOREIGN PATENT DOCUMENTS

| | | |
|---|---|---|
| EP | 1749473 | 2/2007 |
| WO | WO0048507 | 8/2000 |
| WO | WO0217798 | 3/2002 |
| WO | WO0247559 | 6/2002 |
| WO | 2009037479 | 3/2009 |
| WO | 2005104945 | 11/2015 |

TOOL AND METHOD FOR DIGITAL ACQUISITION OF A TIBIAL MECHANICAL AXIS

CROSS-REFERENCE TO RELATED APPLICATIONS

The present is a Continuation of U.S. patent application Ser. No. 12/872,469 filed Aug. 31, 2010, the entire content of which is incorporated herein by reference.

TECHNICAL FIELD

The present application relates generally to computer-assisted surgery systems and, more particularly, to a surgical tool and method used to determine a tibial mechanical axis using such a CAS system.

BACKGROUND

Computer-assisted surgery (CAS) systems which employ inertial-based or micro-electro-mechanical sensor (MEMS), trackable members continue to be developed.

One of the principal steps in navigating a bone with inertial sensors is to determine a coordinate system of the bone relative to the sensors, such as to be able to determine the orientation of the bone. For the tibia, the orientation of the bone is determined by its mechanical axis.

When traditional optical CAS navigation systems are used, the determination of the tibial mechanical axis can be achieved, for example, by using two optical bone sensors fixed to the bone at spaced apart locations, each optical sensor having six degrees of freedom (DOF) (i.e. 3 DOF in position and 3 DOF in orientation). When using trackable members having inertial sensors in an inertial-based CAS system, however, the inertial sensors do not necessarily provide 6 DOF. While the missing DOF can be calculated if necessary using integrated gyroscope and accelerometer readings, for example, a simpler and more efficient manner to digitize the mechanical axis of a tibia is nonetheless sought.

Therefore, there remains a need for an improved surgical tool which is used in conjunction with a CAS system in order to digitally acquire the mechanical axis of the tibia using readily identifiable anatomical reference points.

SUMMARY

In accordance with one aspect of the present application, there is provided a digitizing tool adapted for digitizing a mechanical axis of a tibia using a computer-assisted surgery system, the tool comprising: an upper mounting end and a lower mounting end interconnected by an alignment rod extending therebetween, the upper mounting end being releasably fastenable to an upper reference point on a tibial plateau and the lower mounting end having a self-centering malleoli engaging mechanism thereon, the self-centering malleoli engaging mechanism including opposed caliper arms each having a malleolus clamp, the caliper arms being displaceable in a common plane relative to each other for clamping engagement with the medial and lateral malleoli, such that a midpoint between the caliper arms corresponds to a lower reference point defined midway between the medial and lateral malleoli; and at least one trackable member mounted to the alignment rod of the tool, the trackable member producing at least orientation information and being adapted for communication with the computer-assisted surgery system; wherein the alignment rod is aligned parallel with the mechanical axis of the tibia which extends between the upper reference point and the lower reference point when the tool is mounted on the tibia.

In accordance with a further aspect of the present application there is also provided a method for determining a mechanical axis of a tibia using an inertial-based computer assisted surgery system and a tibial digitizer having an upper mounting end, a lower mounting end and an alignment rod extending therebetween, the tibial digitizer including at least one inertial sensor in communication with the computer assisted surgery system, the method comprising: determining an upper reference point on a tibial plateau of the tibia, the upper reference point being an entry point of the mechanical axis; fastening the upper mounting end of the tibial digitizer to the tibial plateau at the upper reference point; fastening the lower mounting end of the tibial digitizer to medial and lateral malleoli of the ankle; determining a lower reference point located at a midpoint between the medial and lateral malleoli by identifying a corresponding midpoint on the lower mounting end of the tibial digitizer; adjusting an orientation of the alignment rod such that the alignment rod is aligned with an anatomical landmark on the tibia; and using the computer assisted surgery system to determine the mechanical axis of the tibia extending between the upper and lower reference points by providing at least orientation data of the tibial digitizer to the computer assisted surgery system using the inertial sensor.

There is further provided, in accordance with another aspect of the present application, a digitizing tool adapted for acquiring a mechanical axis of a tibia using a computer assisted surgery system, the digitizing tool comprising: spaced apart upper and lower mounting ends each having at least one mounting point respectively adapted to be secured to a tibial plateau and malleoli of the tibia, the mounting point of the upper mounting end being fastenable to the tibial plateau at a mechanical axis entry point defining an upper reference point; an alignment rod extending between and interconnecting the upper and lower mounting ends, the alignment rod defining a longitudinal axis and being disposed a common distance from the mounting points on the upper and lower mounting ends, at least one trackable member mounted to the alignment rod, the trackable member producing at least orientation-based data for at least two degrees of freedom in orientation of the trackable member and thus of the alignment rod; the lower mounting end including a self-centering malleoli engagement mechanism having a base portion pivotally connected to the alignment rod and opposed caliper arms slideably mounted on the base portion for displacement relative to each other in a plane transverse to the longitudinal axis of the alignment rod, wherein the caliper arms, when displaced towards each other, are adapted to abut the most medial and lateral points on the malleoli to clamp the self-centering malleoli engagement mechanism in place thereto; and wherein a midpoint between the caliper arms of the self-centering malleoli engagement mechanism corresponds to a lower reference point located at a midpoint between the most medial and lateral points on the malleoli, and the mechanical axis extends between the lower reference point and the upper reference point at said common distance from the alignment rod which is aligned parallel thereto.

DETAILED DESCRIPTION

The term "CAS" is used herein to refer to computer-assisted surgery.

The term "MEMS" is used herein to refer to micro-electro-mechanical sensors, for example, but not limited to, accelerometers, gyroscopes and other inertial sensors.

The present surgical tool and method will be generally described herein with respect to use of the device in conjunction with an inertial-based CAS system 100 employing trackable members having inertial-based sensors, such as the MEMS-based system and method for tracking a reference frame disclosed in U.S. Patent Application No. 61/309,585 filed on Mar. 2, 2010, and the MEMS-based system and method for planning/guiding alterations to a bone disclosed in U.S. patent application Ser. No. 12/410,884 filed Mar. 25, 2009, the entire contents of both of which are incorporated herein by reference. However, it is to be understood that the tool and method described herein may also be used with other CAS systems.

The surgical tool 10 (best seen in FIG. 4) is a "tibial digitizer", which may, in a particular embodiment, be provided for use with an inertial-based CAS system in order to digitally acquire the mechanical axis of the tibia. Thus, as will be described, the tibial digitizer 10 includes trackable members thereon which, in at least the presently described embodiment, include inertial sensors for communication with the inertial-based CAS system. These inertial sensors are referred to as MEMS sensors or MEMS trackable members in the embodiment described below, however it is to be understood that the term "MEMS" or "MEMS sensor" as used herein may include any combination of inertial-based tracking circuitry, for example including MEMS, gyroscopes, accelerometers, compasses, electronic tilt sensors, etc., all of which are able to detect orientation changes. However, although particularly developed for use with inertial based sensors and an inertial-based CAS system, it is also to be understood that the present tibial digitizer may similarly be used with other CAS systems, and thus may include trackable members thereon which are not exclusively inertial-based. As will be described in further detail below, the tibial digitizer 10 is used to digitally acquire the mechanical axis of the tibia, in a manner which is quick, accurate and easily repeatable, by using readily identifiable anatomical references on the tibia to position the tibial digitizer in place, as will be first described with reference to FIGS. 1-3.

Figure 2:
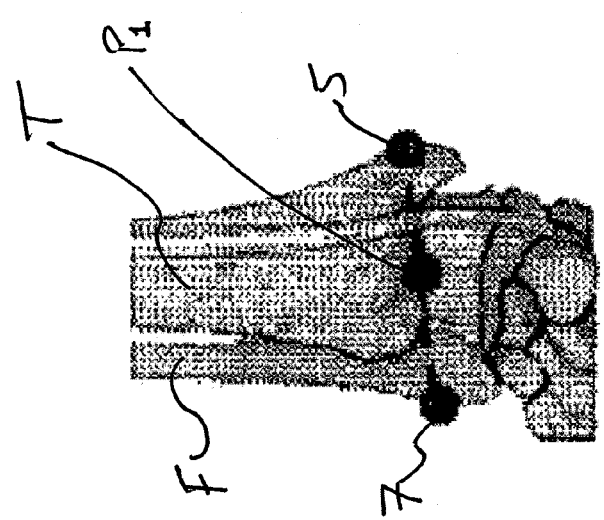
FIG. 2 is a partial side view of an ankle region showing the malleoli and a midpoint therebetween used as a first reference point for determining the mechanical axis of the tibia.
Figure 1:
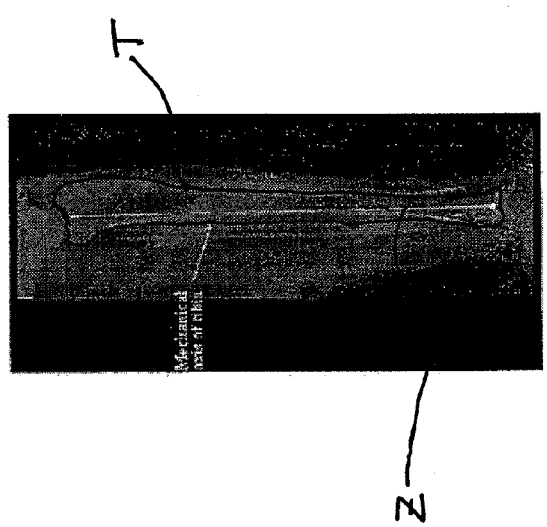
FIG. 1 is an x-ray of a side view of a tibia showing the tibial mechanical axis.

As seen in FIG. 1, the mechanical axis Z of the tibia T may in fact be defined by two reference points located from known landmarks on the bone. As seen in FIG. 2, the first, or lower, of these two reference points is the midpoint $P_1$ between the most medial point 5 on the medial malleolus and the most lateral point 7 of the lateral malleolus (on the fibula F) which make up the ankle. The second, or upper, of these two reference points is the mechanical axis entry point $P_2$ on the tibial plateau 9. The generally accepted mechanical axis entry point on the tibial plateau may be used. However, in one particular embodiment, the mechanical axis entry point $P_2$ on the tibial plateau 9 may be defined as being at the intersection of two axes on the tibial plateau, the first axis Y being centered medial-laterally and the second axis X being located one-third anterior and two-thirds posterior. Thus, the mechanical axis Z of the tibia T is defined between the two reference points $P_1$ and $P_2$, which can be located and acquired by the CAS system for the tibia T using the identified anatomical landmarks which are located by the tibial digitizer tool 10.

Figures 4, 5:
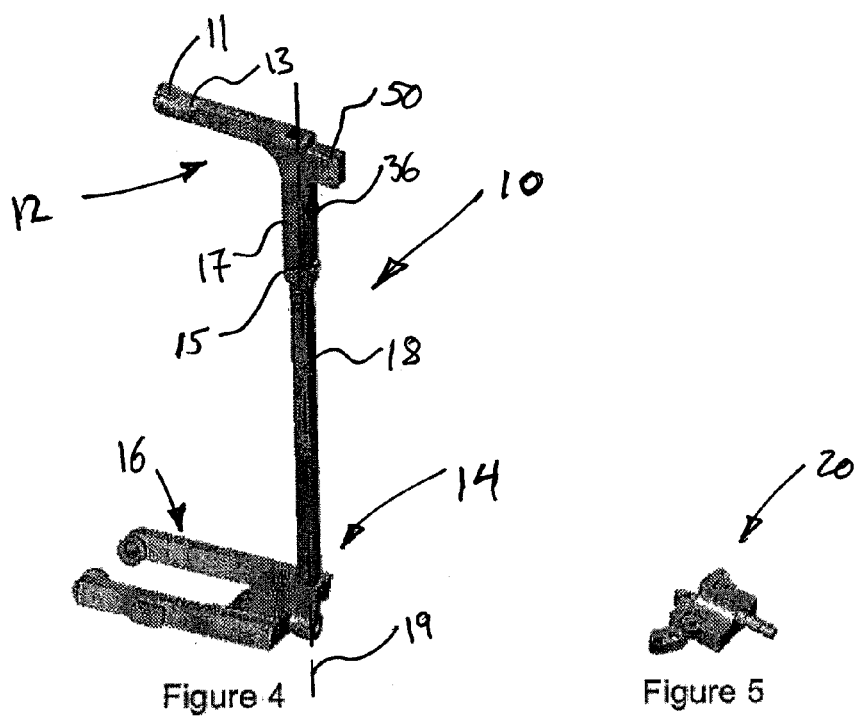
FIG. 4 is a perspective view of a tibial digitizer tool of the present application used to acquire the mechanical axis of the tibia.
FIG. 5 is a perspective view of a tibial reference which is installed on the tibial plateau in alignment with the mechanical axis of the tibia using the tibial digitizer tool of FIG. 4.

Referring now to FIGS. 4 to 8, the tibial digitizer 10 will be described in further detail. As seen in FIG. 4, the tibial digitizer 10 generally includes an upper mounting end 12 and a lower mounting end 14, interconnected by an alignment rod 18. The upper mounting end, or upper portion, 12 is removably fastened to the tibial plateau using a tibial reference 20 (see FIG. 5). The lower mounting end, or lower portion, 14 engages the ankle region, and more specifically the malleoli, using a self-centering malleoli engaging mechanism 16, as will be described in further detail. In one embodiment, the alignment rod 18 which interconnects the upper and lower portions of the tibial digitizer is adjustable in length along its longitudinal axis 19, such as to permit the upper and lower portions 12, 14 to be axially displaced relatively to each other along this longitudinal axis 19, while being nonetheless capable of being fixed in place once a desired length of the tibial digitizer 10 is reached. For example, the alignment rod 18 may be a telescoping rod, and/or may, as depicted in FIG. 4, be slideably received within a mating tube 17 of the upper portion 12, in order to permit longitudinal adjustment along the axis 19. This longitudinal adjustment permits the overall size of the tibial digitizer tool 10 to be adjusted as required in order to fit a large range of tibia lengths. A locking mechanism 15 is provided on the upper portion 12 in order to fix the sliding rod 18 of the lower portion 14 and the tube 17 of the upper portion 12 in place with respect to each other, thereby maintaining the desired overall axial length of the tibial digitizer 10 such that it accommodates the tibia being operated on. The alignment rod 18 is, in the embodiment described herein, pivotally mounted to both the upper and lower mounting ends 12,14, such as to permit an orientation of the alignment rod 18 to be adjustable once the upper and lower mounting ends are fastened in place to the tibia.

Figure 9:
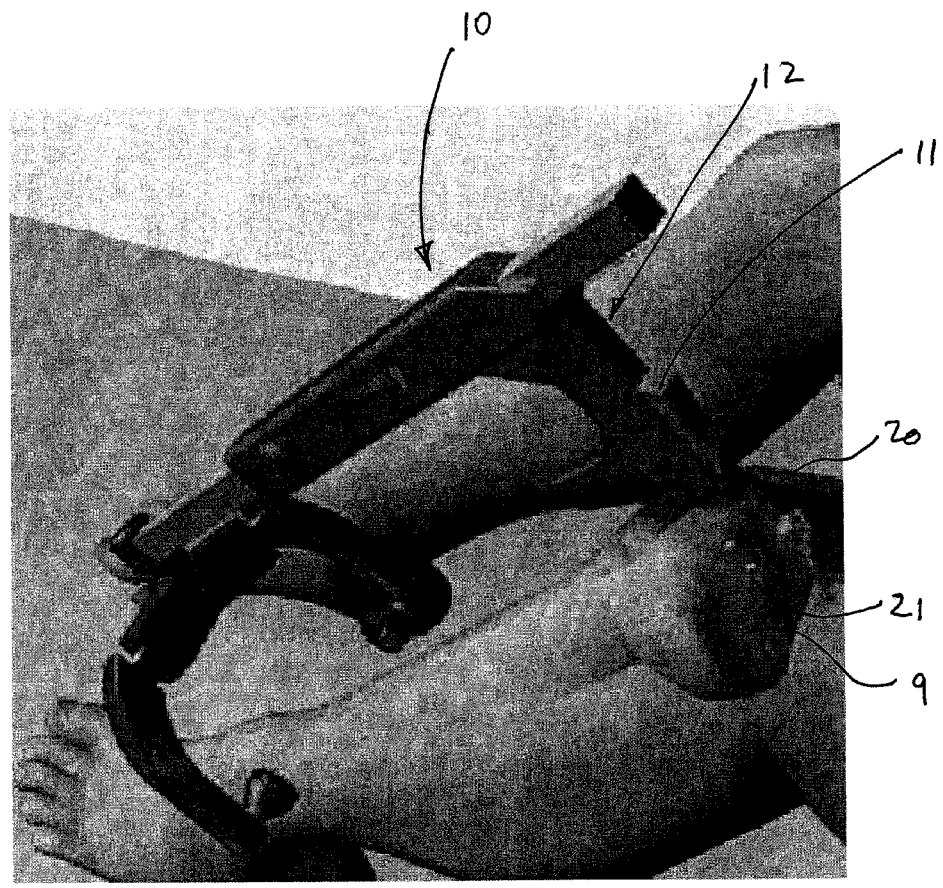
FIG. 9 is a perspective view of the tibial reference tool being mounted to the tibial plateau at a mechanical axis entry point thereon.

The tibial reference 20 shown in FIG. 5 is fastened to the tibial plateau 9 (as shown in FIG. 9 for example). More specifically, the tibial reference 20 is fastened to the tibial plateau 9 at the upper reference point $P_2$ (see FIG. 3) corresponding to the mechanical axis entry point using a suitable number of pins or other bone fasteners (for example two or three fasteners 21 may be used). At least one of these fasteners 21 is fixed to tibial plateau 9 at the mechanical axis entry point $P_2$ such that the mechanical axis entry point of the tibia is at a known position with regard to the tibial reference 20, and therefore to the tibial digitizer 10 once engaged to the tibial reference 20. The tibial reference 20 may additionally serve, subsequent to the digital acquisition of the tibial axis as described herein, as a mounting point and platform for deployment of a cutting guide or other cutting reference block used during a knee replacement surgery to resect a portion of the tibia in preparation for the installation of a tibial knee prosthesis.

In this regard, the innermost end 13 of the upper portion 12 of the tibial reference 10 includes a releasable engagement mechanism 11 thereon, which is used to releasably fasten the tibial digitizer 10 to the tibial reference 20 in order to removably fasten the tibial digitizer 10 to the tibia. Thus, with the tibial reference 20 pinned to the mechanical axis entry point $P_2$ on the tibial plateau 9, the uppermost end of the tibial digitizer 10 is fastened in place to the tibia at the upper tibial axis entry point $P_2$.

The releasable engagement mechanism 11 between the tibial digitizer 10 and the tibial reference 20 may include at least two rotational adjustments, namely one in the flexion-extension direction and one in the varus-valgus direction. These two rotational adjustments permit the entire tibial digitizer 10 to be pivoted in these two degrees of freedom, as will be described in further detail below, while the upper portion 12 of the tibial digitizer 10 nonetheless remains fastened in place to the tibial plateau 9. As will be seen, the adjustment in the flexion-extension and varus-valgus planes permits the tibial digitizer 10 to be adjusted as required when the malleoli engagement mechanism 16 of the lower portion 14 of the tool is engaged in place on the ankle.

Figure 6:
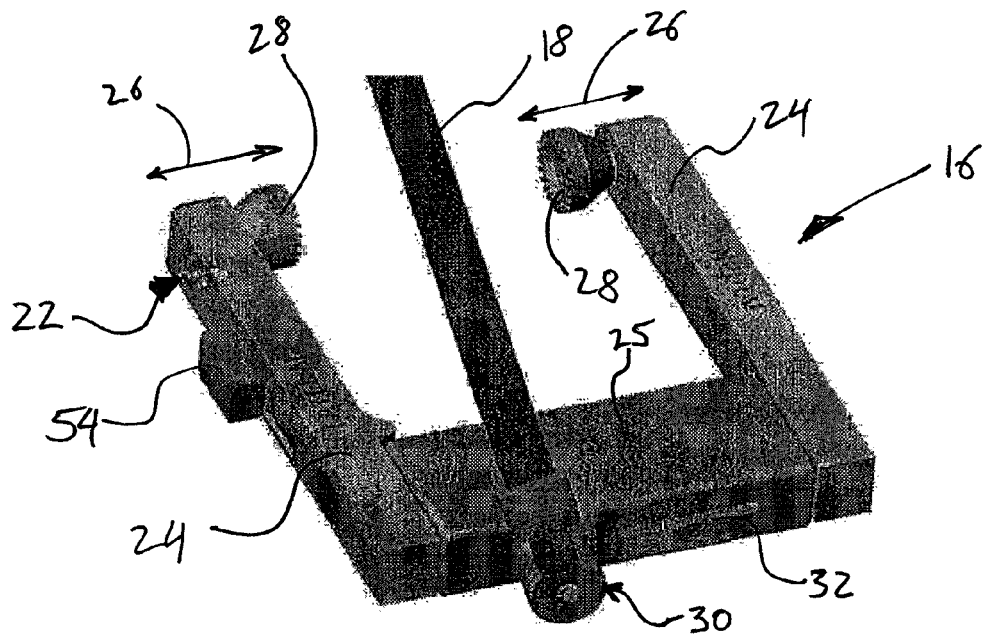
FIG. 6 is a perspective view of a self-centering malleoli engaging mechanism on a lower portion of the tibial digitizer tool of FIG. 4.

Referring now to FIG. 6, the self-centering malleoli engaging mechanism 16 is disposed at the lower end of the rod 18 to form the lower portion 14 of the tibial digitizer 10. The self-centering mechanism 16 comprises a clamp-like caliper 22 having a base portion 25, pivotally mounted to a lower end of the rod 18 by a pivotal connection 30, and opposed caliper arms 24 which are slideably mounted on the base portion 25 for displacement relative to each other in a plane that is substantially transverse to the longitudinal axis 19 of the rod 18, i.e. the axis 19 intersects the plane within which the caliper arms move at any angle that may include, but is not limited to, 90 degrees. In at least one possible embodiment, the caliper arms 24 are displaced in a substantially medial-lateral direction 26 in order to bring the malleoli clamps 28, disposed on the inner-most remote ends of each caliper arm 24, into abutted engagement with the most medial point on the medial malleolus and the most lateral point on the lateral malleolis. Accordingly when so engaged, the self-centering mechanism 16 is clamped in place on the malleoli and thereby able to define a mid-point between the malleoli while clamped in place thereon, given that a midpoint between the caliper arms 24 also corresponds to a midpoint between the medial and lateral malleoli. The lower reference point $P_1$ (see FIG. 2) can therefore be identified by the CAS system by identifying the midpoint of the self-centering mechanism 16 on the lower portion 14 of the tibial digitizer 10. In one possible embodiment, at least one of the caliper arms 24 of the self-centering malleoli engaging mechanism 16 includes an inertial-based trackable member 54 thereon, such as to produce orientation data pertaining to at least one degree of freedom in orientation of the caliper arms 24 in their plane of sliding adjustment. This accordingly permits the CAS system in communication with the trackable member 54 to determine the orientation of the caliper arms 24, and thus the entire self-centering malleoli engaging mechanism 16.

Figure 11:
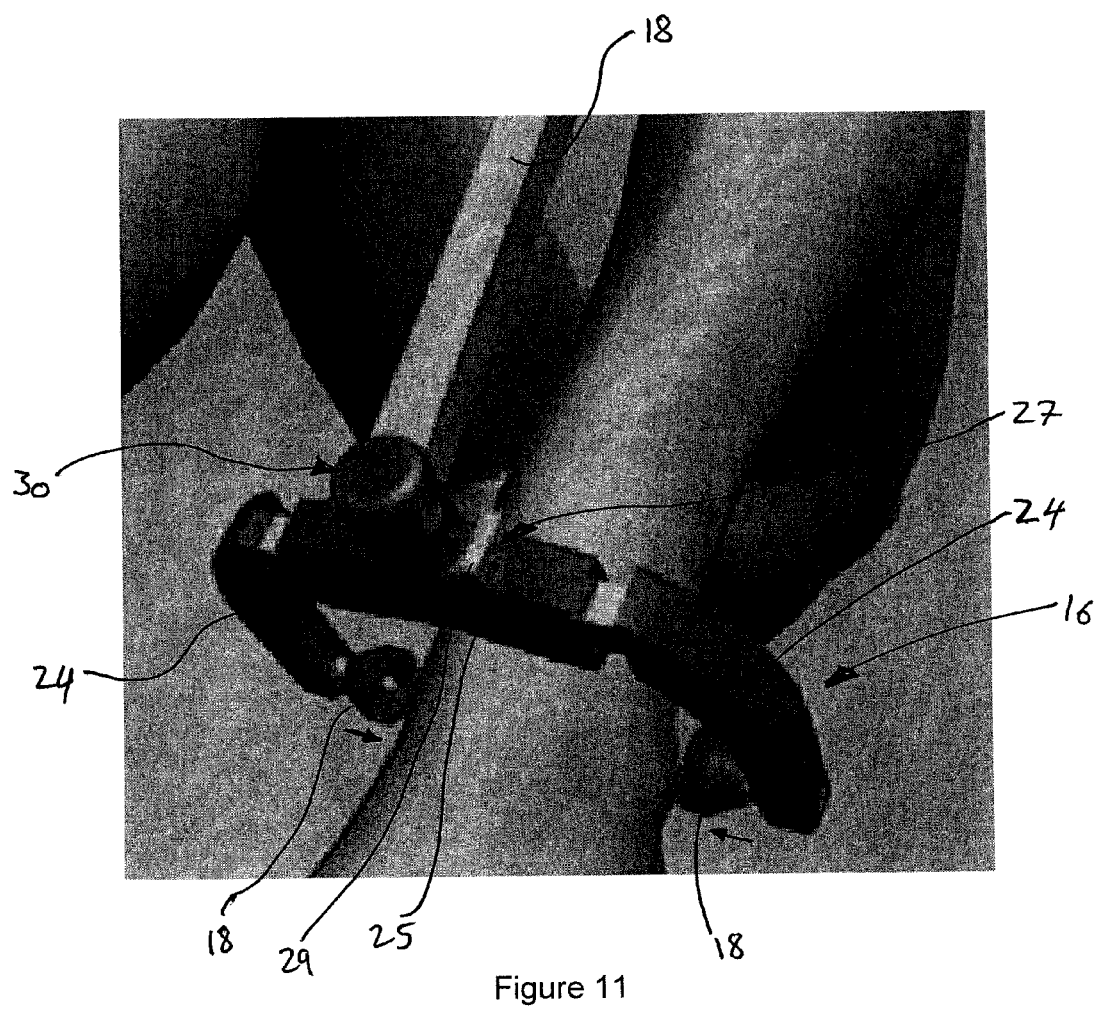
FIG. 11 is a enlarged perspective view of the self-centering malleoli engaging mechanism on the lower portion of the tibial digitizer tool being adjusted to engage the malleoli of the ankle.

In one embodiment, the arms 24 of the caliper 22 may operate in a ratchet-like manner, in that they can be displaced inwardly (i.e. towards each other) until the clamps 28 engage the malleoli, however outward displacement of the caliper arms 24 is prevented unless a locking feature released by the operator. Namely, as seen in FIG. 11, a ratchet mechanism 27 may be provided within the base portion 25 of the self-centering mechanism 16, and the inner ends of each of the caliper arms 24 are engaged by the ratchet mechanism 27 such that inward movement of the caliper arms is permitted but outward movement (i.e. away from the malleoli) is prevented unless a release lever 29 is actuated. Thus, once located and fastened in place on the malleoli, the self-centering mechanism 16 remains fixed in place until such time as the release lever 29 is actuated, thereby permitting the caliper arms 24 to be moved apart and the self-centering mechanism 16 thus released from engagement with the ankle. Alternately, the centering malleoli engaging mechanism may include another type of mechanism permitting the caliper arms to be displaced in an inward direction towards each other without restriction such as to clamp onto the malleoli but restricting movement of the caliper arms in an opposed outward direction unless the locking feature of the mechanism is released. For example, the mechanism may be spring-loaded or otherwise biased in the closed position.

The lower end of the rod 18 is pivotally linked with the self-centering mechanism 16 via a pivot connection 30, which may include a sliding pin displaceable within a mating slot 32 in the base portion 25 of the self-centering mechanism 16. Alternately, the pivot connection 30 may be located in a fixed medial-lateral direction on the base portion 25, while nonetheless still permitting pivotal movement in a varus-valgus plane between the rod 18 and the base 25 of the self-centering mechanism 16.

Figure 12:
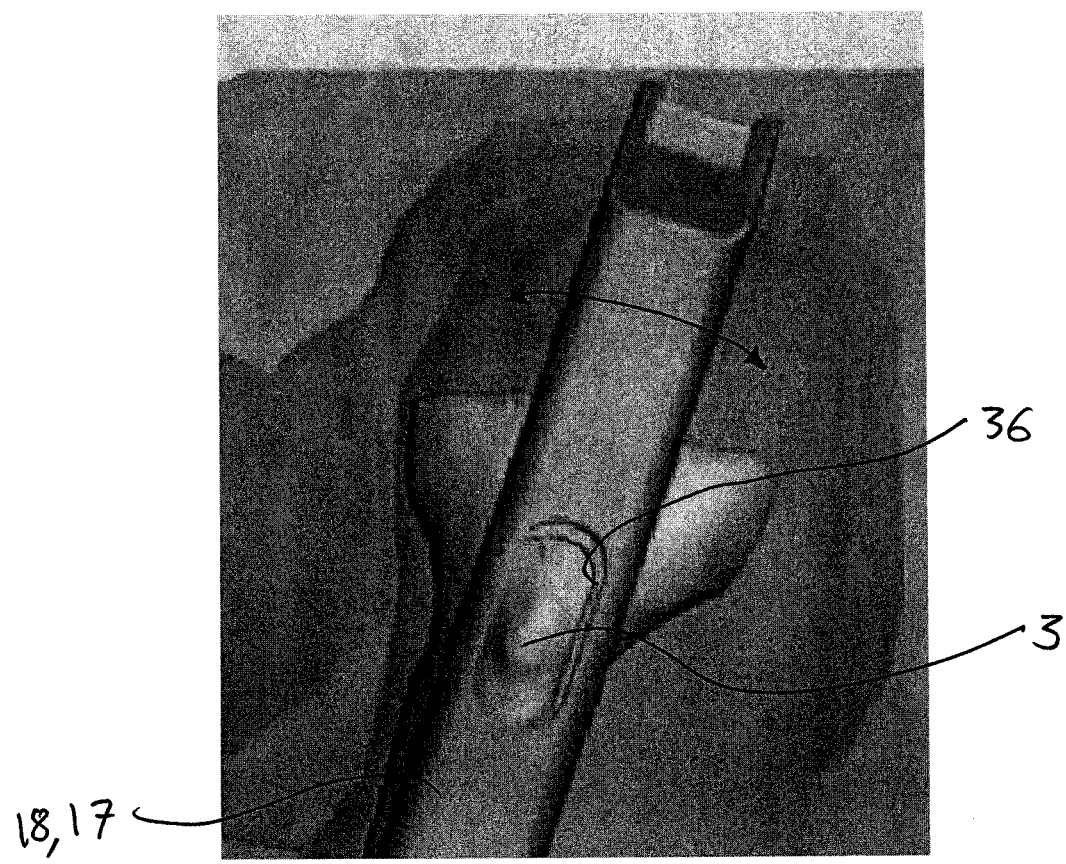
FIG. 12 is an enlarged perspective view of an upper portion of the tibial reference tool being adjusted in a medial-lateral direction such as to visually align the opening in the tibial digitizer tool with the tibial tuberosity which is used as an anatomical landmark.

Once the upper end 12 of the tibial digitizer 10 has been fastened to the tibial reference 20 and the self-centering mechanism 16 of the tibial digitizer's lower portion 14 has been clamped in place on the malleoli, the tibial digitizer 10 is thus fastened to the tibia at both upper and lower ends thereof. As best seen in FIG. 12, the rod 18 of the digitizer may then be rotated, for example in a medial-lateral direction and/or varus-valgus plane, such as to visually align a visual reference guide in the form of a visual guide 36, which in this embodiment is an opening defined through the rod 18 and/or the tube 17 of the tibial digitizer's upper portion 12 within which the rod is received, with a selected anatomical landmark on the tibia. In a particular embodiment, the anatomical landmark used is the tibial tuberosity 3, as shown in FIG. 12. In alternate embodiments, other landmarks may also be used, for example the anterior crest of the tibia, however this may require reconfiguration of the alignment rod and/or the location, shape and/or configuration of the visual markers 36. Accordingly, the visual guide 36 is disposed on the alignment rod 18 in a position corresponding to a proximal-distal location of an anatomical landmark on the tibia used to position and/or align the alignment rod relative thereto. Although in the present embodiment the visual guide 36 is an opening extending through the rod 18 and/or the tube 17, it is to be understood that another suitable visually identifiable guide may be used, for example a reference marker located on an outer surface of the rod and/or tube 17.

When so adjusted, the orientation of the rod 18 is fixed in place, such that it remains in fixed position relative to both the lower end 14 clamped in place to the malleoli and the upper end 12 fixed in place to the tibial plateau via the tibial reference 20, and therefore relative to the tibia as a whole.

At least the orientation of rod 18 of the tibial digitizer 10 may then be determined by the CAS system 100 (FIG. 8), which is in communication with at least one inertial-based trackable member 50 mounted on the rod 18, such as to thereby digitally acquire the mechanical axis Z of the tibia which, as noted below, is now disposed parallel to the tracked rod 18 of the tibial digitizer 10.

Figures 7, 8:
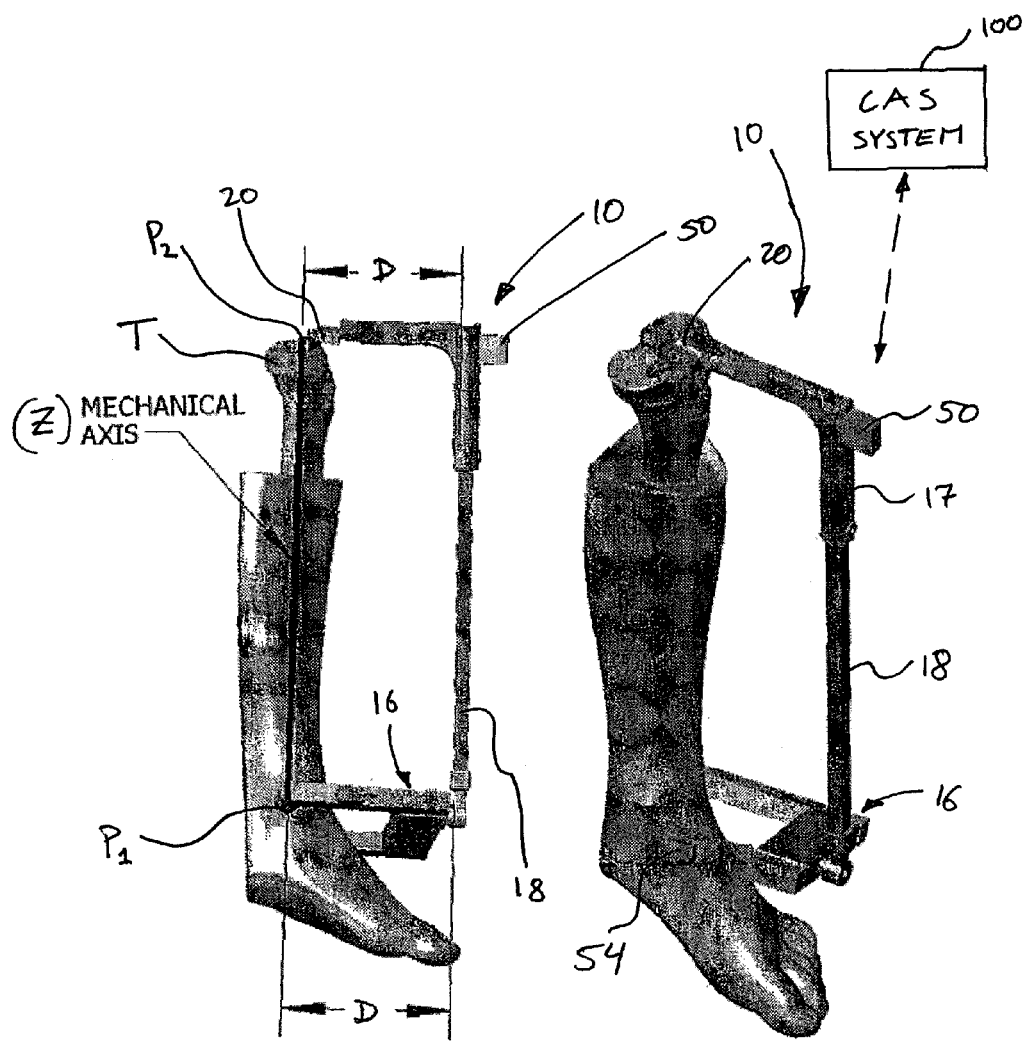
FIG. 7 is a side view of the tibial digitizer and tibial reference mounted to a tibia in order to digitally acquire its mechanical axis using a CAS system in communication therewith.
FIG. 8 is a perspective view of the tibial digitizer and tibial reference mounted to the tibia.

Once adjusted in position as shown in FIGS. 7 and 8, the rod 18 of the tibial digitizer 10 is thereby located at a known distance D away from both the lower reference point $P_1$, located at midpoint of the self-centering mechanism 16, and the upper reference point $P_2$, located at the mechanical axis entry point on the tibial plateau at which the tibial reference 20 is fastened. As such the rod 18 of the tibial digitizer 10 is aligned with, and parallel to, the mechanical axis Z of the tibia. Once in this position and orientation, the MEMS trackable member 50 on the tibial digitizer 10, which is positioned on the rod 18 and/or the tube 17 receiving the rod 18, the digitizer 10 can therefore be used by the CAS system 100 in communication with the MEMS sensor 50 to determine the location and orientation in space of the mechanical axis Z of the tibia T when the tibial digitizer 10 is mounted to the tibia as described herein. The tibial digitizer 10 accordingly permits the CAS system to digitally acquire and subsequently track the mechanical axis Z of the tibia.

Referring now to FIGS. 9 to 14, the method of installing the tibial digitizer 10 as set out in FIG. 15 will now be described in further detail.

Figure 10:
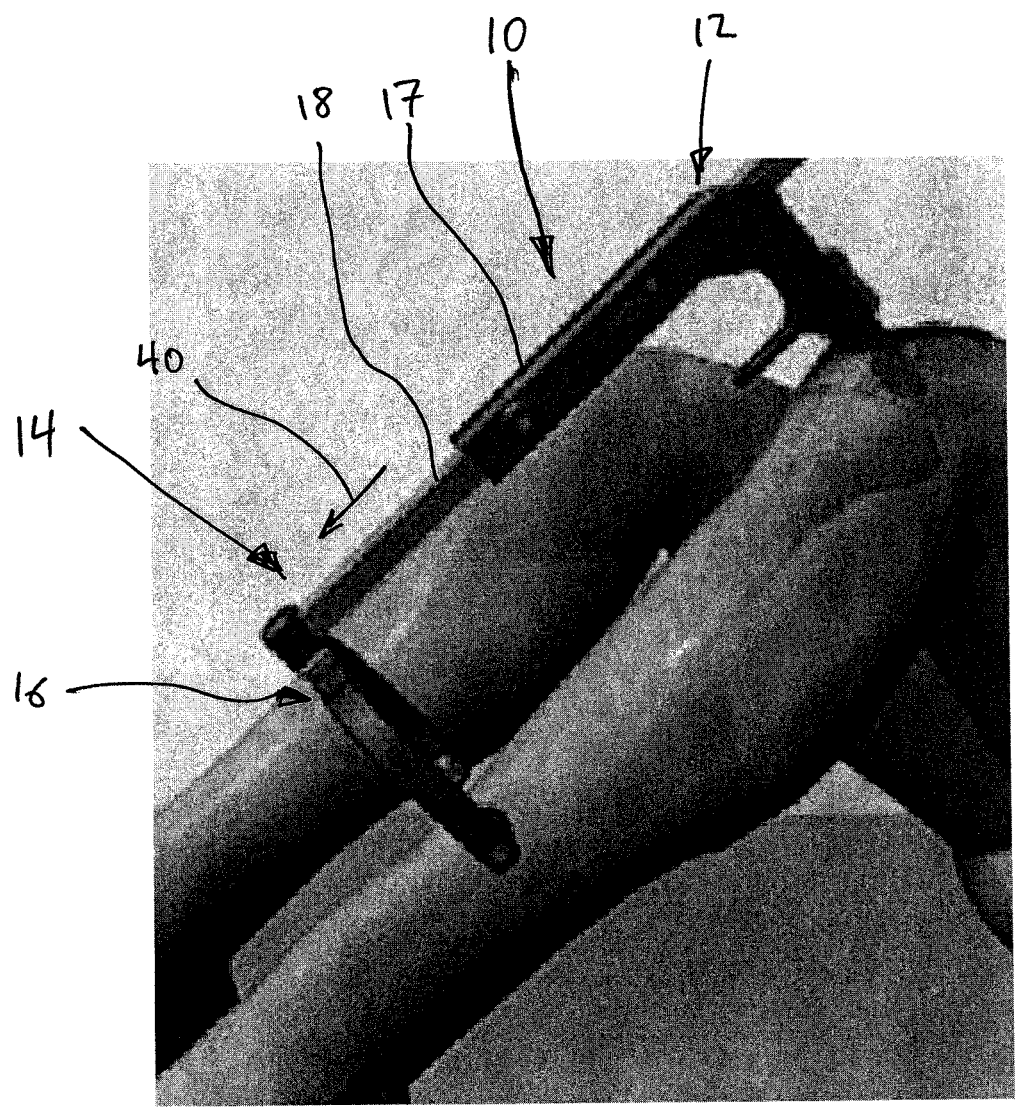
FIG. 10 is a side perspective view of a lower portion of the tibial reference tool being axially displaced towards the ankle.

As seen in FIG. 9, once the tibial reference 20 is fastened in place to the selected mechanical axis entry point $P_2$ using one or more fasteners 21 (in one exemplary embodiment two or three are used), the upper portion 12 of the tibial digitizer 10 may then be engaged to the tibial reference 20 by the attachment mechanism 11. Once the upper portion 12 of the tibial digitizer is fastened in place at the upper end of the tibia, as seen in FIG. 10, the lower portion 14 of the tibial digitizer, including the self-centering malleoli engaging mechanism 16, is axially displaced in direction 40 towards the ankle by sliding the rod 18 out of the tube 17 of the tibial digitizer's upper portion 12. As seen in FIG. 11, once the self-centering mechanism 16 on the lower portion of the tibial digitizer is proximate the ankle, the rod 18 may be fixed in position within the tube 17 using the locking mechanism 15 (not seen in FIG. 11) and the self-centering mechanism 16 of the lower portion 14 of the tibial digitizer may be adjusted as described above in order for the malleoli clamps 28 on the caliper arms 24 to be aligned with, and moved towards each other until they engage, the medial and lateral malleoli. The self-centering mechanism 16 therefore permits the caliper arms 24 to be displaced inwardly such that the clamps 28 engage the malleoli, while the central portion 25 of the self-centering mechanism 16 remains pivotally connected to the rod 18 via the pivot connection 30. By closing the caliper arms 24 and engaging the malleoli, the self-centering mechanism 16 is thereby able to identify the midpoint between the two clamps 28, which accordingly corresponds to the lower reference point $P_1$ defined at the midpoint between the most medial point 5 on the medial malleolus and the most lateral point 7 on the lateral malleolus. The lower reference point $P_1$ of the mechanical axis is thus defined and identified in space by the CAS system, such that the mechanical axis Z of the tibia may be determined.

As seen in FIG. 12, once the upper and lower ends of the tibial digitizer 10 are fastened to the bone, medial-lateral displacement and/or varus-valgus rotational adjustment of the rod 18 (not seen in FIG. 12), and tubular portion 17 with which the rod is mated, is permitted by the pivoting connections at either end of the tibial digitizer. This medial-lateral displacement and/or varus-valgus rotational adjustment is used to visually align and center the openings 36, defined in the tubular portion 17 of the tibial digitizer's upper portion 12, with the tibial tuberosity 3 on the tibia in order to ensure that the rod 18 and tube 17 of the tibial digitizer 10 are aligned with and parallel to the mechanical axis of the tibia, as described above with reference to FIG. 7.

Figure 13:
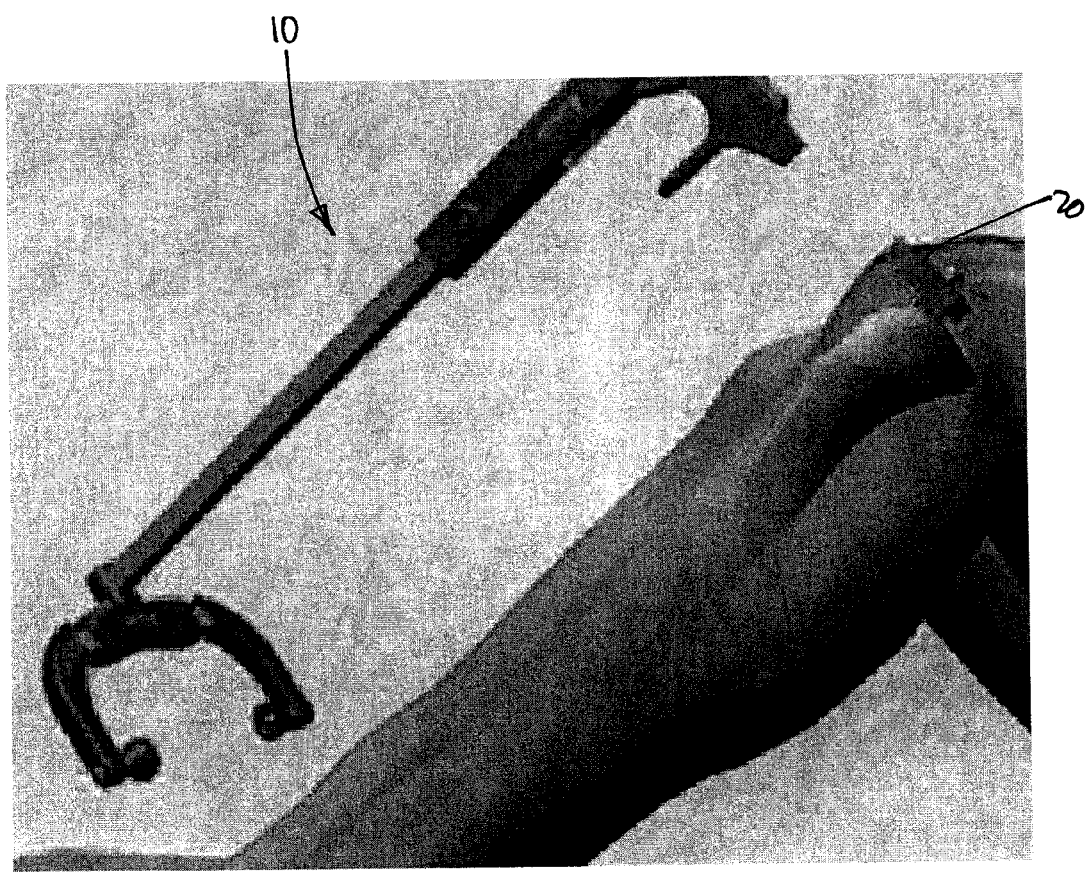
FIG. 13 is a side perspective view of the tibial digitizer tool being removed from the tibial reference still fixed to the tibial plateau.
Figure 14:
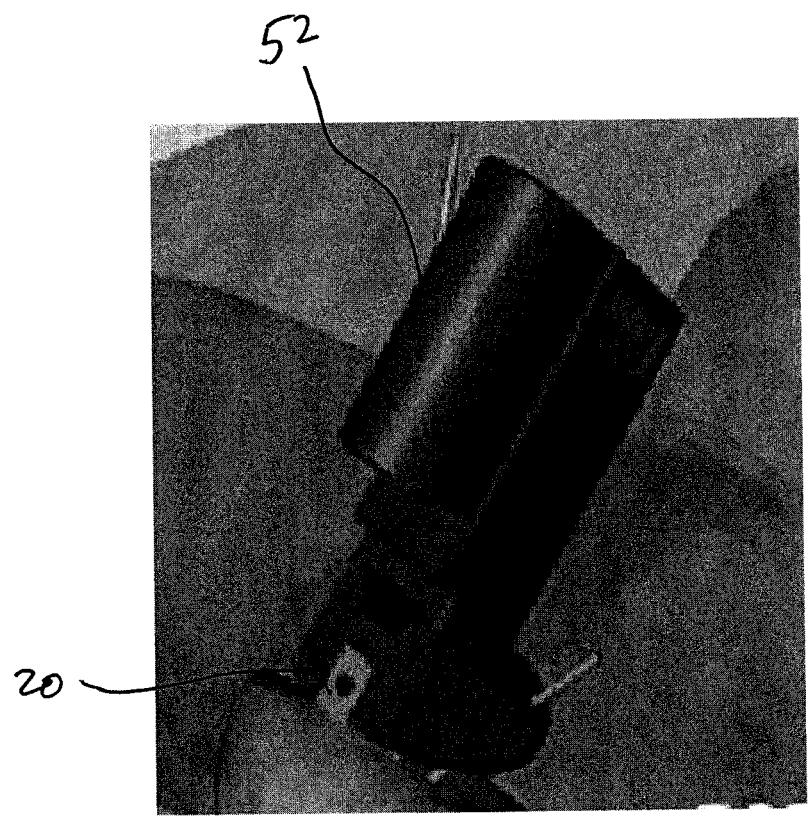
FIG. 14 is an enlarged perspective view of a MEMS sensor of the CAS system being fastened to the tibial reference.

Once in position, the MEMS trackable member(s) 50 on the tibial digitizer 10 provide at least two degrees of freedom information to the CAS system in communication with the tracked tibial digitizer 10, such that the CAS system may then digitally acquire the position and orientation of the mechanical axis of the tibia. Once this is achieved, the tibial digitizer 10 may be disengaged from the tibial reference 20, which remains fastened to the tibial plateau, as shown in FIG. 13. Once the tibial digitizer has been removed, a further MEMS sensor 52 may then be fastened to the tibial reference 20, as shown in FIG. 14. The MEMS bone sensor 52 remains fixed relative to the tibia and relative to the acquired mechanical axis thereof, in order to permit the CAS system to further track the tibia during surgery.

Figure 15:
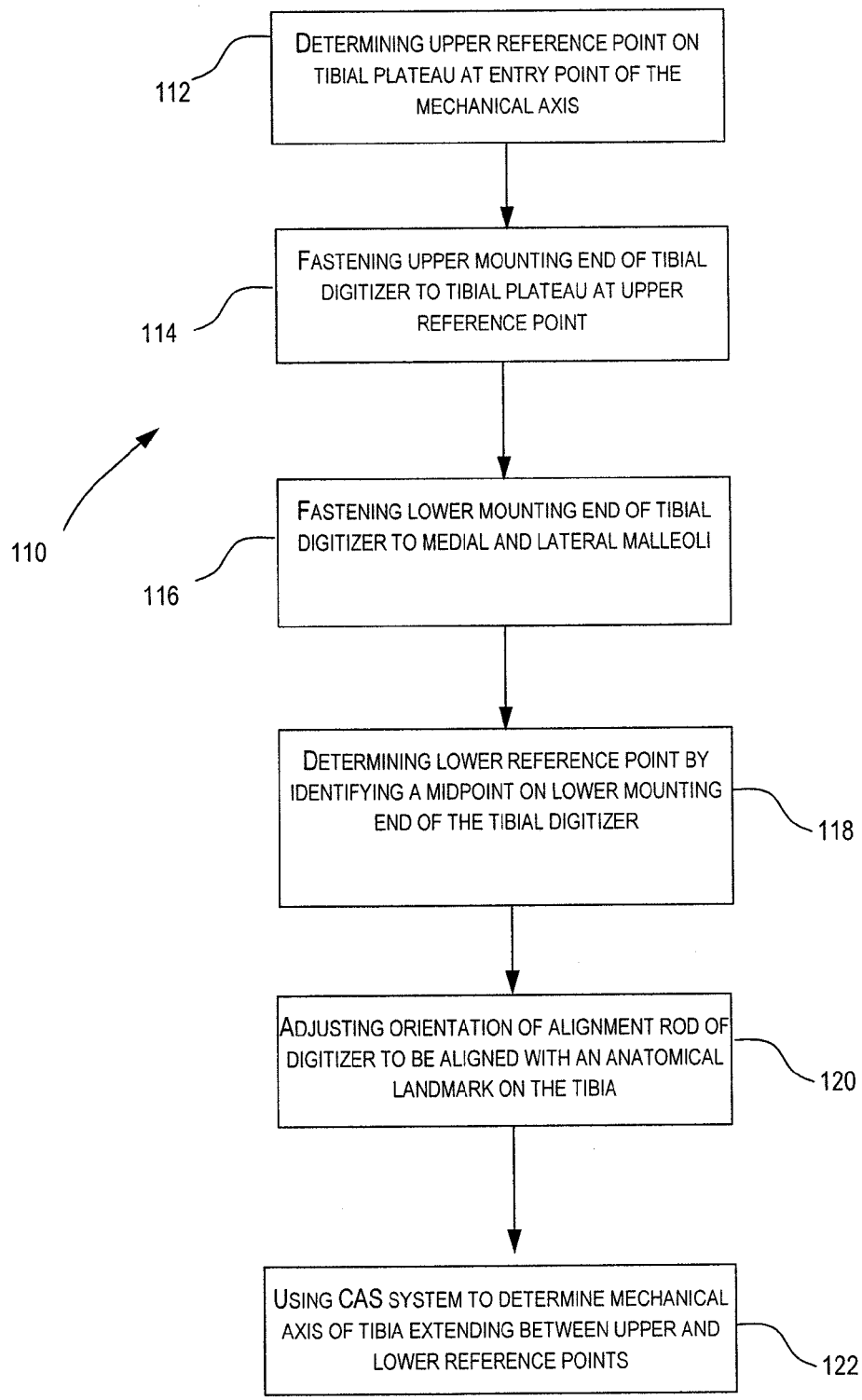
FIG. 15 is a flow chart illustrating a method for determining the mechanical axis of the tibia in accordance with an embodiment of the present disclosure.

As set out in FIG. 15, and with reference to FIGS. 4-14 and the preceding description of the tibial digitizer 10, the method 110 of determining a mechanical axis of a tibia using an inertial-based computer assisted surgery system and the present tibial digitizer will now be summarized. As noted above, the tibial digitizer 10 includes an upper mounting end 12, a lower mounting end 14 and an alignment rod 18 extending therebetween. The tibial digitizer 10 includes at least one inertial sensor 50 in communication with the inertial-based computer assisted surgery system 100. A first step 112 of the method 110 includes determining an upper reference point $P_2$ on a tibial plateau 9 of the tibia T, the upper reference point $P_2$ being an entry point of the mechanical axis Z. Step 114 of the method includes fastening the upper mounting end 12 of the tibial digitizer 10 to the tibial plateau 9 at the upper reference point $P_2$, as shown in FIG. 9. Step 116 of the method includes fastening the lower mounting end 14 of the tibial digitizer 10 to medial and lateral malleoli of the ankle, as shown in FIG. 11. Step 118 of the method includes determining a lower reference point $P_1$ located at a midpoint between the medial and lateral malleoli by identifying a corresponding midpoint on the lower mounting end 14 of the tibial digitizer 10. Step 120 of the method includes adjusting the orientation of the alignment rod 18 such that it is aligned with an anatomical landmark on the tibia, for example the tibial tuberosity 3, as shown in FIG. 12. Step 122 of the method includes using the CAS system to determine the mechanical axis Z of the tibia, which extends between the upper and lower reference points, by providing at least orientation data of the tibial digitizer 10 to the CAS system using the inertial sensor 50.

The step 122 may also include determining at least orientation of the tibial digitizer 10 using the computer assisted surgery system 100 such as to digitally acquire the mechanical axis Z of the tibia based on the determined orientation of the alignment rod 18 and the known distance D (see FIG. 7) between the trackable member 50 on the tibial digitizer 10 and the mechanical axis.

The step 120 may also include orienting the alignment rod 18 to be parallel with the mechanical axis Z of the tibia extending between the determined upper and lower reference points $P_2$, $P_1$.

Figure 3:
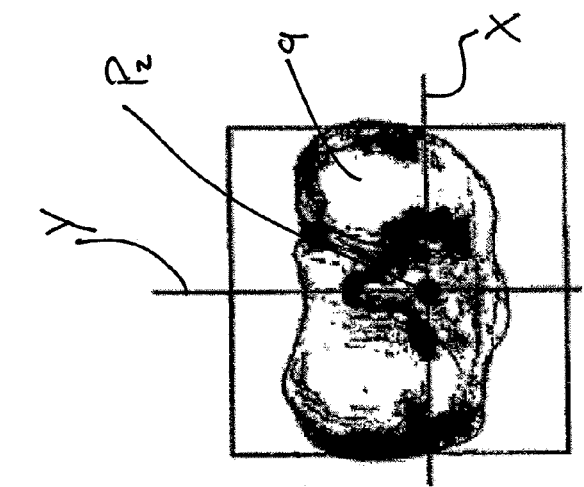
FIG. 3 is a top plan view of the tibial plateau, showing the entry point thereon used as a second reference point for determining the mechanical axis of the tibia.

The step 112 may also include locating the entry point of the mechanical axis on the tibial plateau 9 by identifying an intersection point, which corresponds to upper reference point $P_2$, between a first axis Y centered medial-laterally on the tibial plateau 9 and a second axis X located one-third anterior and two-thirds posterior, as seen in FIG. 3. These first and second axis X,Y lie in a common plane transverse to the mechanical axis Z.

The step 116 may include using the self-centering clamp mechanism 16 on the lower mounting end 14, and inwardly displacing the opposed caliper arms 24 of the self-centering clamp mechanism 16 towards each other until they abut and are clamped to the medial and lateral malleoli 5,7 of the ankle.

The step 120 may include aligning the anatomical landmark on the tibia with a visual guide defined on the alignment rod 18, and more particularly displacing the alignment rod 18 until the tibial tuberosity 3, which is the anatomical landmark used in one embodiment, is centered within opening 36 of the visual guide. This adjustment and displacement of the alignment bar 18 may include at least one of a translation in a medial-lateral direction and a rotation in a varus-valgus plane, or any combination thereof.

The step 110 as described herein is, in one particular embodiment, performed entirely on a bone model or cadaver.

The present application features CAS trackable members, such as the MEMS trackable member 50 for example, which are inertial-based sensors and which therefore include inertia-based tracking circuitry. The tracking circuitry within these trackable members may feature micro-electromechanical sensors (MEMS), gyroscopes, accelerometers or other types of inertial sensors (electrolytic tilt sensors, compasses) to detect orientation changes, for instance of the tibial digitizer 10. Therefore, while MEMS sensors 50, 52 are described herein as one particular embodiment of the present disclosure, it is understood that any suitable inertial-based sensor may be used. These inertial sensors may include, for example and without being limited to: tri-axial gyroscopic sensors in an orthogonal or semi-orthogonal configuration as well as tri-axial accelerometer sensors in an orthogonal or semi-orthogonal configuration.

The CAS system 100 in communication with the inertial sensors of the trackable members 50, 52, 54 which constitute the tracking members obtains planar (i.e. orientation) information and optionally position information directly from the inertial MEMS sensors of these trackable members, rather than having to compute this information as would be required when using conventional optical tracking members. In other words, the inertial sensors provide at least two degrees of freedom in orientation, and optionally up to three degrees of freedom in position.

Referring now to FIGS. 16 to 19, a tibial digitizer 210 in accordance with an alternate embodiment operates much as per the tibial digitizer 10 described above and depicted in FIGS. 4 to 8.

The tibial digitizer 210 generally includes an upper mounting end 212 and a lower mounting end 214, interconnected by an alignment rod 218. The upper mounting end, or upper portion, 212 is removably fastened to the tibial plateau using a tibial reference 220. The lower mounting end, or lower portion, 214 engages the ankle region, and more specifically the malleoli, using a self-centering malleoli engaging mechanism 216. In this embodiment, the upper mounting end 212 is displaceable on the alignment rod 218 along its longitudinal axis, such as to permit the upper and lower portions 12, 14 to be axially displaced relatively to each other along this longitudinal axis, while being nonetheless capable of being fixed in place once a desired relative position of the upper and lower mounting ends are reached. This longitudinal adjustment permits the overall size of the tibial digitizer tool 210 to be adjusted as required in order to fit a large range of tibia lengths. A locking mechanism 215 (see FIG. 19) is provided on the upper portion 212 in order to fasten the upper portion 212 in place on the rod 218, thereby maintaining the desired overall axial length of the tibial digitizer 210 such that it accommodates the tibia being operated on. The alignment rod 218 is, in this embodiment, pivotally mounted to both the upper and lower mounting ends 212,214, such as to permit an orientation of the alignment rod 218 to be adjustable once the upper and lower mounting ends are fastened in place to the tibia.

The tibial reference 220 is adapted to be fastened in place to the tibia at the mechanical axis entry point on the tibial plateau. The tibial reference 220 is releasably fastened to the upper portion 212 of the tibial digitizer 210, and permits at least two rotational adjustments, namely one in the flexion-extension direction and one in the varus-valgus direction. These two rotational adjustments permit the entire tibial digitizer to be pivoted in these two degrees of freedom while the upper portion 212 of the tibial digitizer 210 nonetheless remains fastened in place to the tibial plateau via the tibial reference.

Figure 16:
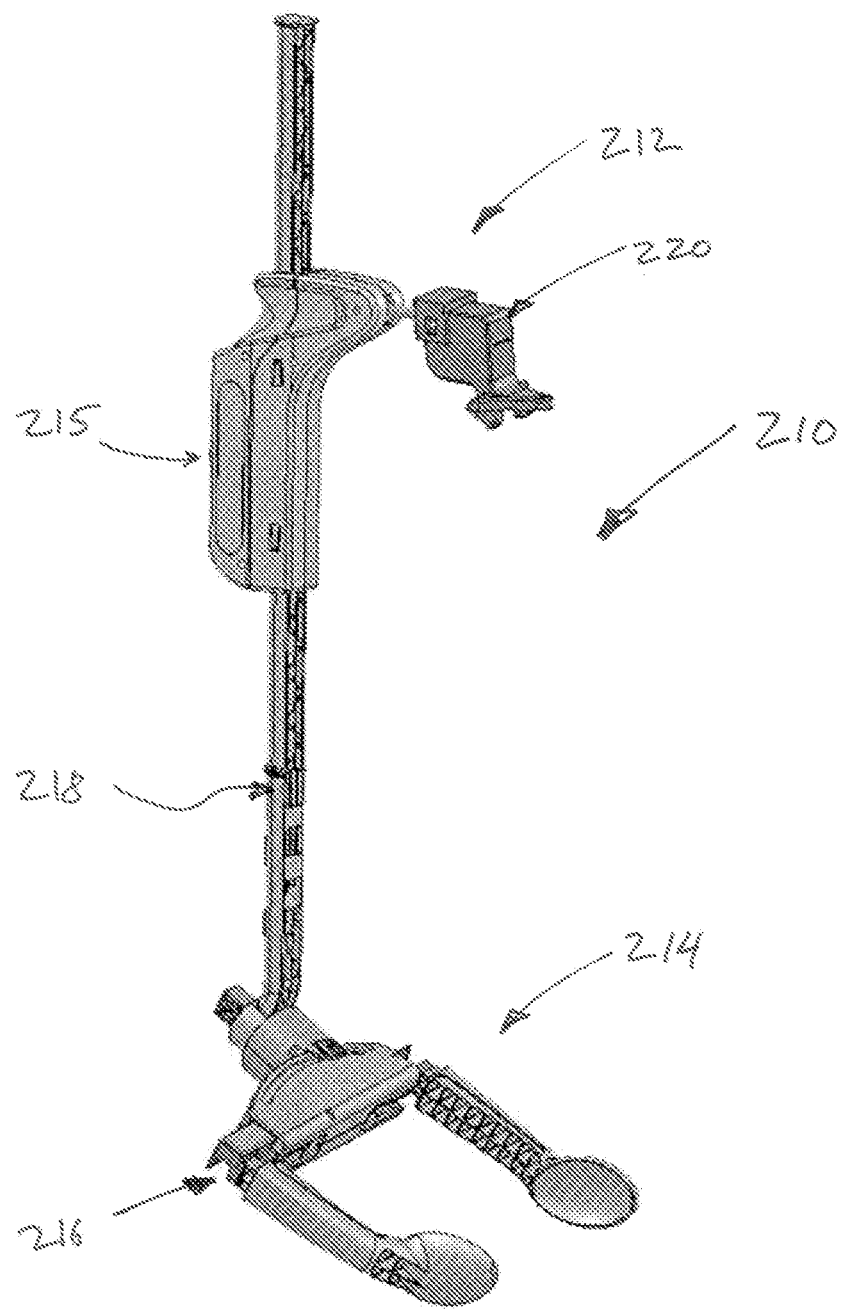
FIG. 16 is a perspective view of an alternate embodiment of a tibial digitizer tool used to acquire the mechanical axis of a tibia.
Figure 17:
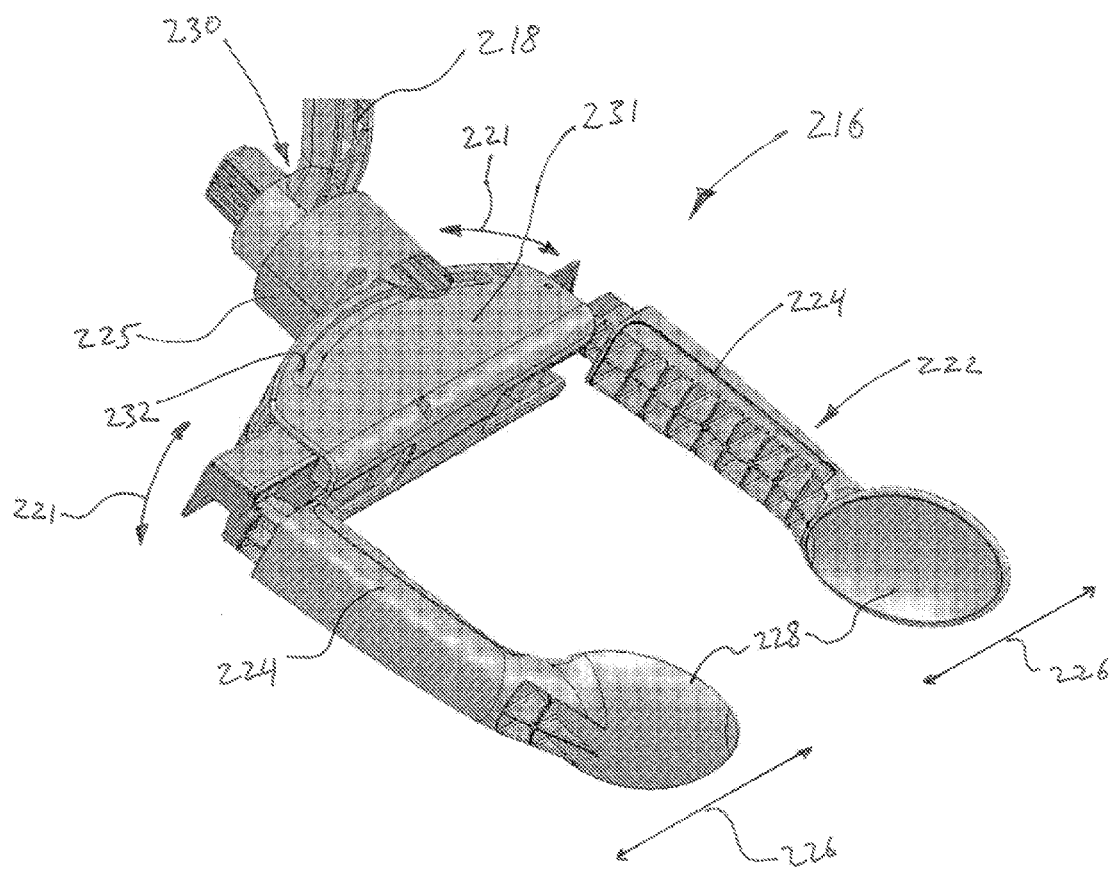
FIG. 17 is an enlarged front perspective view of a self-centering malleoli engaging mechanism on a lower portion of the tibial digitizer tool of FIG. 16.
Figure 18:
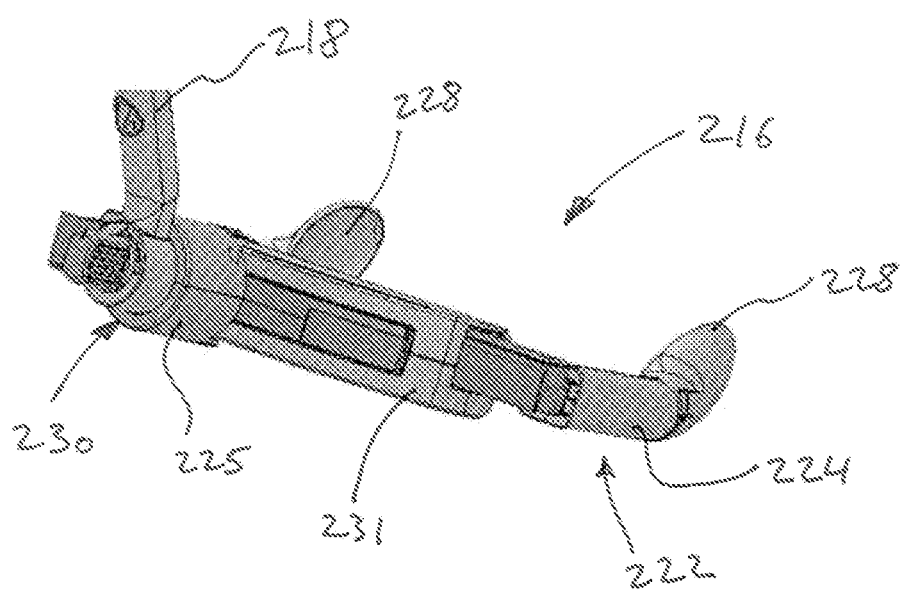
FIG. 18 is an enlarged rear perspective view of the self-centering malleoli engaging mechanism on a lower portion of the tibial digitizer tool of FIG. 16.
Figure 19:
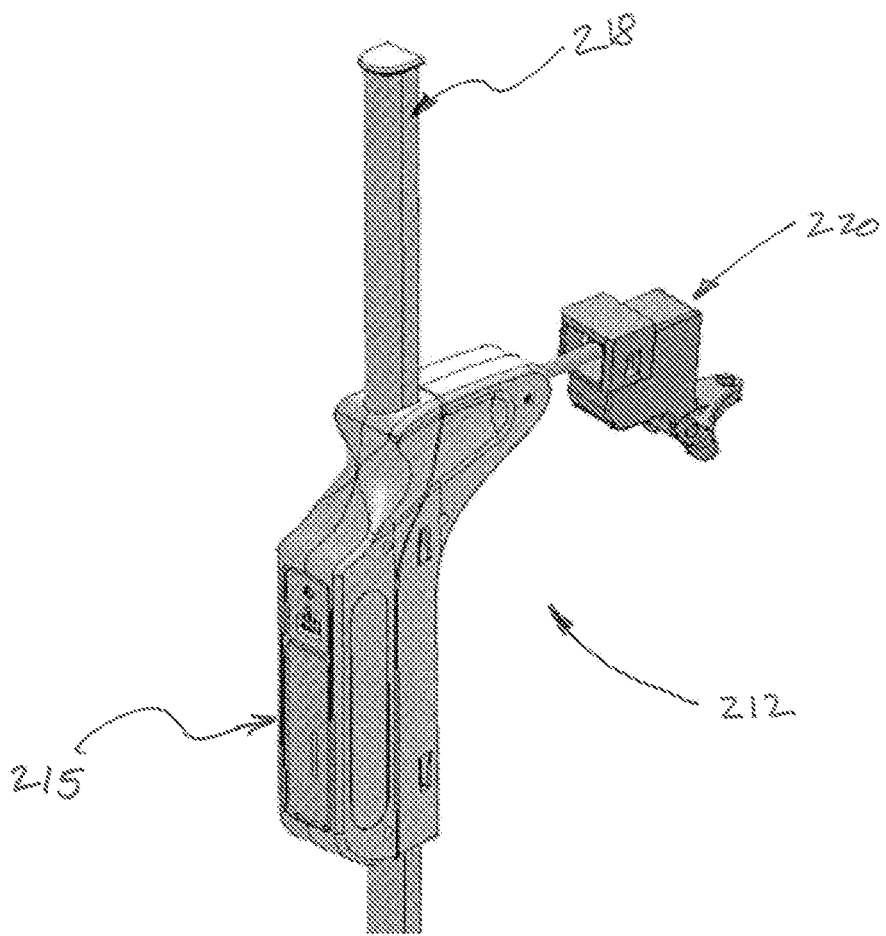
FIG. 19 is an enlarged perspective view of top portion of the tibial digitizer tool of FIG. 16.

Referring now to FIGS. 16 to 17, the self-centering malleoli engaging mechanism 216 is similar to the self-centering malleoli engaging mechanism 16 described above. The self-centering malleoli engaging mechanism 216 comprises a clamp-like caliper 222 having a base portion 225, pivotally mounted to a lower end of the rod 218 by a pivotal connection 230, a central caliper body portion 231 and a pair of opposed caliper arms 224 on either side of the central caliper body portion 231. The caliper arms 224 are slideably mounted on the central caliper body 231 for displacement relative to each other within a common plane that may be substantially transverse to the longitudinal axis of the rod 218. The caliper arms 224 are may therefore be displaced in a substantially medial-lateral direction 226 in order to bring the malleoli clamps 228, disposed on the inner-most remote ends of each caliper arm 224, into abutted engagement with the most medial point on the medial malleolus and the most lateral point on the lateral malleolis. In an alternate configuration, however, the caliper arms 224 may be pivotably brought towards each other rather than remaining relatively parallel to each other when displaced within their common plane, as in the case in the present embodiment. Regardless, when the two caliper arms 224 are brought towards each other until they abut the two malleoli, the self-centering mechanism 216 is clamped in place on the malleoli and thereby able to define a mid-point between the malleoli while clamped in place thereon, given that a midpoint between the caliper arms 224 also corresponds to a midpoint between the medial and lateral malleoli. The central caliper body portion 231 is further adjustable relative to the base portion 225 via a pivoting adjustment, such that the entire caliper sub-assembly may be pivoted in the angular direction 221 within the above-mentioned common plane that is transverse to the longitudinal axis of the alignment rod 218. The pivoting adjustment may include other configurations, but in the present embodiment includes a sliding pin disposed on the base portion 225 which is slidably displaceable within a mating slot 232 in the base portion 25 of the self-centering mechanism 16. The caliper arms 224 of the self-centering melleoli engaging mechanism 216 may include one or more of the inertial-based trackable members described above.

The self-centering mechanism 216 includes a mechanism which permits the arms 224 of the caliper 222 to be displaced in an inward direction towards each other without restriction while at least restricting movement of the caliper arms in an opposed outward direction unless a locking feature of the mechanism is released. This mechanism which permits only one way direction, or which at least provides less resistance to movement in one direction, may include for example a ratchet mechanism and a spring-loaded mechanism. In the case of a ratchet-mechanism, the caliper arms 224 can be displaced inwardly (i.e. towards each other) until the clamps 228 engage the malleoli, however outward displacement of the caliper arms 224 is prevented unless a locking feature is released by the operator. Alternately, in the case of a spring-loaded mechanism, the caliper arms may be inwardly biased, such as by a spring or other equivalent member, such that their tend to return to their inwardly directed clamped position unless they are released via a deactivated locking feature or are otherwise separated by the user.

The presently described tibial digitizer tool 10 is therefore used to digitize the mechanical axis of the tibia, thereby creating an orientation reference such as to enable subsequent tracking of the acquired mechanical axis of the tibia by the CAS system, using for example the trackable member 52 fastened to the tibia post-digitization of the mechanical axis. The inertial or MEMS trackable members of the digitizer accordingly provide two or three DOF tracking circuitry or can alternately be calibrated to perform orientation tracking, such that the CAS system in communication with these sensors is able to digitally acquire the mechanical axis of the tibia and thus subsequently track the tibia during surgery.

The presently described MEMS-based trackable members may include both a gyroscope sensor and an accelerometer sensor, and thus may provide readings to the CAS system from both types of sensors. The gyroscope sensor and the accelerometer sensor within the trackable members may each provide at least orientation data along three degrees of freedom.

The embodiments of the invention described above are intended to be exemplary only. Those skilled in the art will therefore appreciate that the forgoing description is illustrative only, and that various alternatives and modifications can be devised without departing from the scope of the present invention, which is intended to be limited solely by the scope of the appended claims. Accordingly, the present description is intended to embrace all such alternatives, modifications and variances which fall within the scope of the appended claims.

The invention claimed is:

1. A digitizing tool adapted for digitizing a mechanical axis of a tibia using a computer-assisted surgery system, the tool comprising:
   an upper mounting end and a lower mounting end interconnected by an alignment rod extending therebetween, the upper mounting end being releasably fastenable to an upper reference point on a tibial plateau and the lower mounting end having a self-centering malleoli engaging mechanism thereon, the self-centering malleoli engaging mechanism including opposed caliper arms each having a malleolus clamp, the caliper arms being displaceable in a common plane relative to each other for clamping engagement with the medial and lateral malleoli, such that a midpoint between the caliper arms corresponds to a lower reference point defined midway between the medial and lateral malleoli; and
   at least one trackable member mounted to the alignment rod of the tool, the trackable member producing at least orientation information and being adapted for communication with the computer-assisted surgery system;
   wherein the alignment rod is aligned parallel with the mechanical axis of the tibia which extends between the upper reference point and the lower reference point when the tool is mounted on the tibia.

2. The tool as defined in claim 1, wherein the trackable member includes an inertial sensor.

3. The tool as defined in claim 2, wherein the inertial sensor produces at least orientation-based data for at least two degrees of freedom in orientation of the sensor and thus of the alignment rod on which the sensor is mounted.

4. The tool as defined in claim 2, wherein the inertial sensor includes one or more micro-electro-mechanical sensors, accelerometers, gyroscopes, compasses, and electronic tilt sensors.

5. The tool as defined in claim 1, wherein the self-centering malleoli engaging mechanism includes at least a second trackable member thereon, the second trackable member produces orientation-based data of the self-centering malleoli engaging mechanism.

6. The tool as defined in claim 5, wherein the second trackable member is mounted on one of the caliper arms of the self-centering malleoli engagement mechanism.

7. The tool as defined in claim 1, wherein the self-centering malleoli engaging mechanism includes a mechanism permitting the caliper arms to be displaced in an inward direction towards each other without restriction such as to clamp onto the malleoli but at least restricting movement of the caliper arms in an opposed outward direction unless a locking feature of the mechanism is released.

8. The tool as defined in claim 7, wherein the mechanism includes one of a ratchet mechanism and a spring-loaded mechanism.

9. The tool as defined in claim 1, wherein the alignment rod defines a longitudinal axis extending therethrough, the alignment rod being adjustable in length relative to the longitudinal axis such as to vary a distance between the upper and lower mounting ends.

10. The tool as defined in claim 9, wherein the alignment rod telescopes such as to adjust the length thereof.

11. The tool as defined in claim 1, wherein the alignment rod is pivotally mounted to both the upper and lower mounting ends, such as to permit an orientation of the alignment rod to be adjustable in at least a varus-valgus plane once the upper and lower mounting ends are fastened in place to the tibia.

12. The tool as defined in claim 1, wherein the alignment rod includes a visual guide thereon, the visual guide being disposed on the alignment rod in a proximal-distal position corresponding to a location of an anatomical landmark on the tibia used to align the alignment rod.

13. The tool as defined in claim 12, wherein the visual guide includes an opening extending through the alignment rod within which the anatomical landmark is visually centered to align the alignment rod with the mechanical axis of the tibia.

14. A digitizing tool adapted for acquiring a mechanical axis of a tibia using a computer assisted surgery system, the digitizing tool comprising:
spaced apart upper and lower mounting ends each having at least one mounting point respectively adapted to be secured to a tibial plateau and malleoli of the tibia, the mounting point of the upper mounting end being fastenable to the tibial plateau at a mechanical axis entry point defining an upper reference point;
an alignment rod extending between and interconnecting the upper and lower mounting ends, the alignment rod defining a longitudinal axis and being disposed a common distance from the mounting points on the upper and lower mounting ends, at least one trackable member mounted to the alignment rod, the trackable member producing at least orientation-based data for at least two degrees of freedom in orientation of the trackable member and thus of the alignment rod;
the lower mounting end including a self-centering malleoli engagement mechanism having a base portion pivotally connected to the alignment rod and opposed caliper arms slideably mounted on the base portion for displacement relative to each other in a plane transverse to the longitudinal axis of the alignment rod, wherein the caliper arms, when displaced towards each other, are adapted to abut the most medial and lateral points on the malleoli to clamp the self-centering malleoli engagement mechanism in place thereto; and
wherein a midpoint between the caliper arms of the self-centering malleoli engagement mechanism corresponds to a lower reference point located at a midpoint between the most medial and lateral points on the malleoli, and the mechanical axis extends between the lower reference point and the upper reference point at said common distance from the alignment rod which is aligned parallel thereto.

15. The digitizing tool as defined in claim 14, wherein the trackable member includes an inertial sensor.

16. The digitizing tool as defined in claim 15, wherein the inertial sensor includes one or more micro-electro-mechanical sensors, accelerometers, gyroscopes, compasses, and electronic tilt sensors.

17. The digitizing tool as defined in claim 14, wherein the self-centering malleoli engaging mechanism includes at least a second trackable member thereon having a second inertial sensor, the second inertial sensor producing at least orientation-based data of the self-centering malleoli engaging mechanism for one or more degrees of freedom in orientation of the second inertial sensor independently of the first inertial sensor.

18. The digitizing tool as defined in claim 17, wherein the second inertial sensor is mounted on one of the caliper arms of the self-centering malleoli engagement mechanism.

19. The digitizing tool as defined in claim 14, wherein the self-centering malleoli engaging mechanism includes a mechanism which permits the caliper arms to be displaced in an inward direction towards each other without restriction for clamping onto the malleoli but at least restricting movement of the caliper arms in an opposed outward direction unless a locking feature of the mechanism is released.

20. The digitizing tool as defined in claim 19, wherein the mechanism includes one of a ratchet mechanism and a spring-loaded mechanism.

21. The digitizing tool as defined in claim 14, wherein the alignment rod is longitudinally adjustable such as to vary a length thereof.

22. The digitizing tool as defined in claim 21, wherein the alignment rod telescopes to provide longitudinal adjustment between the upper and lower ends along the longitudinal axis.

23. The digitizing tool as defined in claim 14, wherein at least an orientation of the alignment rod is adjustable in at least a varus-valgus plane once the upper and lower ends are fastened in place to the tibia.

24. The digitizing tool as defined in claim 14, wherein the alignment rod is pivotally mounted to both the upper and lower mounting ends, permitting orientation of the alignment rod to be adjustable once the upper and lower mounting ends are fastened in place to the tibia.

* * * * *